United States Patent [19]
Caille et al.

[11] Patent Number: 5,474,996
[45] Date of Patent: Dec. 12, 1995

[54] PYRIMIDINE DERIVATIVES

[75] Inventors: Jean-Claude Caille, Paris; Stanislas Didierlaurent, Lagny Sur Marne; Jean-Paul Vevert, Pantin, all of France

[73] Assignee: Roussel Uclaf, France

[21] Appl. No.: 888,750

[22] Filed: May 22, 1992

[30] Foreign Application Priority Data

May 23, 1991 [FR] France .................... 9106203

[51] Int. Cl.⁶ .................... A61K 31/505; C07D 239/26
[52] U.S. Cl. .................... 514/256; 514/222.2; 514/270; 544/122; 544/123; 544/242; 544/335
[58] Field of Search .................... 544/3, 53, 54, 544/58.6, 60, 96, 97, 122, 123, 295, 242, 298, 299, 301, 302, 303, 315, 316, 317, 318, 319, 320, 321, 322, 326, 327, 329, 333, 334, 335; 514/222.2, 228.8, 256, 269, 270, 274

[56] References Cited

U.S. PATENT DOCUMENTS 5,100,897  3/1992  Allen et al. .................... 514/269

FOREIGN PATENT DOCUMENTS 0407342  6/1990  European Pat. Off. .
0419048  8/1990  European Pat. Off. .

OTHER PUBLICATIONS

Bru—Magniez et al., Chem. Abstract, 116(25)2556278, 1992.
Copy of Chem. Abstracts vol. 75, 1971 (3 pages) #s 151753X, 49022W, 190562b.
Copy of Feb., 1990 Reaction Article, pp. 295–305. J. Heterocyclic Chemistry, 27, 295–305, 1990.

Primary Examiner—Yogendra N. Gupta
Attorney, Agent, or Firm—Bierman and Muserlian

[57] ABSTRACT

Novel pyrimidine derivatives of the formula

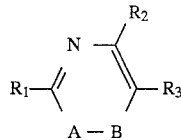

in which:

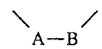

represents:
either a group:

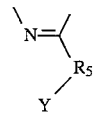

or a group:

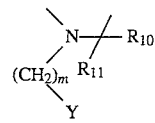

having angiotensin II inhibiting activity.

8 Claims, No Drawings

PYRIMIDINE DERIVATIVES

STATE OF THE ART

Relevant prior art includes European patents No. 0,407, 342 and No. 0,419,048, U.S. Pat. No. 4,824,846, J. of Heterocyclic Chemistry, Vol. 27, No. 2, 1990, Chem. Abs., No. 75 (1971), No. 151,753-X and No. 490,022w and Chem. Abs., No. 104 (1986), No. 109,562b.

OBJECTS OF THE INVENTION

It is an object of the invention to provide the novel pyrimidines of formula I and a process for their preparation.

It is another object of the invention to provide novel angiotensin II inhibiting compositions and a novel method of inhibiting angiotensin II activity in warm-blooded animals.

THE INVENTION

The novel pyrimidines of the invention are compounds selected from the group consisting of all possible racemic, enantiomeric and diastereoisomeric isomer forms of a compound of the formula

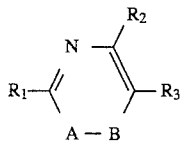

I in which:

represents:
either a group:

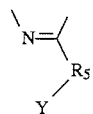

or a group:

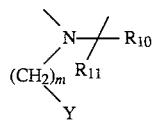

$R_5$ is selected from the group consisting of a single bond, —NH—, —O—$(CH_2)_m$—, —S—$(CH_2)_m$— and alkylene of 1 to 5 carbon atoms optionally substituted with at least one member of the group consisting of halogen, =O and —OZ, Z is hydrogen or alkyl of 1 to 4 carbon atoms optionally substituted with an amino acid, m is an integer from 0 to 4, Y is —$Y_1$—B—$Y_2$, $Y_1$ is a monocyclic aryl of 5 to 6 ring members or condensed rings of 8 to 10 ring members optionally containing at least one heteroatom chosen from oxygen, nitrogen and sulfur and optionally substituted with at least one substitutent of $R_2$ and $R_3$ other than —$R_5$—Y, B is a single bond between $Y_1$ and $Y_2$ or is selected from the group consisting of

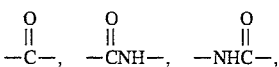

$NH(CH_2)_n$—, —O—$(CH_2)_n$— and —S—$(CH_2)_n$—, n is an integer from 0 to 4, $Y_2$ is selected from the group consisting of hydrogen, halogen, —OH, —CN, —$CF_3$, —$NO_2$, free, salified or esterified carboxy, tetrazole and isoxazole if B is a single bond or has the value of $Y_1$ if B and $Y_2$ have the definition of $Y_1$, $R_{10}$ and $R_{11}$ together form =O or alkylene or are individually selected from the group consisting of hydrogen, halogen, —OH and alkyl, alkoxy and alkylthio of 1 to 6 carbon atoms optionally substituted, $R_1$ is selected from the group consisting of alkyl, alkenyl, alkynyl, alkoxy and alkylthio of up to 10 carbon atoms and cycloalkyl of 3 to 7 carbon atoms, all optionally substituted, $R_2$ and $R_3$ are individually selected from the group consisting of a) —$R_5$—Y, b) hydrogen, halogen, hydroxyl, mercapto, cyano, nitro, sulfo, formyl, benzoyl, acyl of 1 to 12 carbon atoms, free, salified or esterified carboxy, cycloalkyl of 3 to 7 carbon atoms, c) —$S(O)_nR_{12}$, $R_{12}$ is selected from the group consisting of hydroxyl, alkyl, alkenyl, alkoxy, acyloxy, amino, substituted amino, cycloalkyl and aryl, d) alkyl, alkenyl, alkynyl, alkoxy and alkylthio of up to 10 carbon atoms, cycloalkyl of 3 to 7 carbon atoms, all optionally substituted, f) aryl, arylalkyl, arylalkenyl, aryloxy or arylthio, alkyl and alkenyl containing up to 6 carbon atoms and aryl is monocyclic of 5 or 6 ring members or condensed rings of 8 to 10 ring members optionally containing at least one heteroatom chosen from oxygen, nitrogen and sulfur and optionally substituted, g) —$(CH_2)_{m1}$—S—$(O)_{m2}$—X—$R_{17}$, $m_1$ is integer from 0 to 4, $m_2$ is an integer from 0 to 2, and either —X—$R_{17}$— is $NH_2$, or —X— is a single bond or —NH—, —NH—CO— or —NH—CO—NH— and $R_{17}$ is alkyl, alkenyl or aryl optionally substituted,

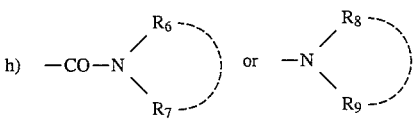

in which either $R_6$ and $R_7$ or $R_8$ and $R_9$ are individually hydrogen, alkyl or alkenyl of up to 6 carbon atoms optionally substituted by at least one halogen or hydroxyl, alkyl or alkenyl of 2 to 6 carbon atoms substituted by alkoxy of 1 to 6 carbon atoms, aryl or arylalkyl in which the alkyl has 1 to 6 carbon atoms and aryl is a monocyclic of 5 or 6 ring members or condensed rings of 8 to 10 ring members optionally containing at least one heteroatom chosen from oxygen, nitrogen and sulfur and optionally substituted by at least one member of the group consisting of halogen, hydroxyl, cyano, trifluoromethyl, nitro, alkyl, alkenyl, alkoxy, alkylthio and acyl of up to 6 carbon atoms, free, salified or esterified carboxy and tetrazolyl, —$(CH_2)_{m1}$—$S(O)_{m2}$—X—$R_{17}$, $m_1$, $m_2$, X and $R_{17}$ have the meanings above, or $R_6$ and $R_7$ or $R_8$ and $R_9$ form respectively together with the nitrogen atom to which they are attached a monocyclic of 5 or 6 ring members or condensed rings of 8 to 10 ring members optionally containing at least one heteroatom chosen from oxygen, nitrogen and sulfur optionally substituted by at least one member of the group consisting of halogen, hydroxyl, cyano, trifluoromethyl, nitro, alkyl, alkenyl, alkoxy, alkylthio and acyl of up to 6 carbon atoms, free, salified or esterified carboxy, tetrazolyl or oxazolyl, or $R_8$ and $R_9$ individually are acyl of a carboxylic acid of up to 6 carbon atoms or aryl or arylsulfonyl in which the aryl has up to 8 carbon atoms optionally substituted by at least one halogen, alkyl, alkoxy, nitro, cyano or trifluoromethyl, or one of $R_8$ or $R_9$ is carbamoyl, alkoxycarbonyl or benzyloxycarbonyl, or $R_8$ and $R_9$ form together with the nitrogen atom to which they are attached phthalimido or succinimido, it being understood that when $R_3$ is —CH$_2$—CH$_2$— or —CH=CH— substituted by

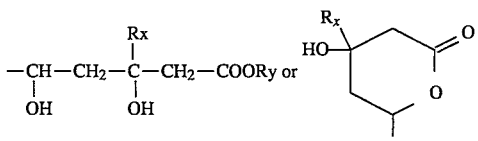

in which Rx is hydrogen or alkyl and Ry is hydrogen, alkyl, aryl, aralkyl or a cation, $R_1$ is not an optionally substituted alkyl or cycloalkyl and their non-toxic, pharmaceutically acceptable salts with acids or bases.

Among the individual substituents that can be carried by:

a) the alkyl, alkenyl, alkynyl, alkoxy, alkylthio and cycloalkyl of $R_1$, $R_2$ and $R_3$, the alkylene, alkyl, alkoxy or alkylthio of $R_{10}$ and $R_{11}$, b) the aryl, arylalkyl, arylalkenyl, aryloxy and arylthio of $R_1$, $R_2$ and $R_3$ and c) the alkyl or aryl of $R_{12}$ are selected from the group consisting of halogen, hydroxyl, cyano, nitro, formyl, acyl or acyloxy of 1 to 6 carbon atoms, benzoyl, carboxy free, salified or esterified by alkyl of 1 to 6 carbon atoms, alkyl and alkenyl of up to 6 carbon atoms optionally substituted by at least one member of the group consisting of halogen, hydroxyl and alkoxy of 1 to 6 carbon atoms, alkoxy and alkylthio of 1 to 6 carbon atoms, aryl and arylalkyl with alkyl of 1 to 6 carbon atoms and the aryl is a monocyclic of 5 or 6 ring members or condensed rings of 8 to 10 ring members optionally containing at least one heteroatom chosen from oxygen, nitrogen and sulfur and optionally substituted by at least one member of the group consisting of halogen, hydroxyl, cyano, trifluoromethyl, nitro, alkyl, alkenyl, alkoxy and acyl of up to 6 carbon atoms, free, salified or esterified carboxy, tetrazolyl or oxazolyl,

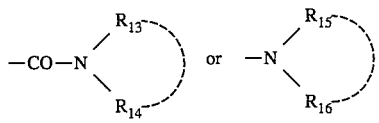

in which either $R_{13}$ and $R_{14}$ or $R_{15}$ and $R_{16}$ are individually selected from the group consisting of hydrogen, alkyl or alkenyl of up to 6 carbon atoms optionally substituted by at least one halogen or hydroxyl, alkyl or alkenyl of 2 to 6 carbon atoms substituted by alkoxy of 1 to 6 carbon atoms, aryl or arylalkyl with alkyl of 1 to 6 carbon atoms and the aryl is monocyclic of 5 or 6 ring members or condensed rings of 8 to 10 ring members optionally containing at least one heteroatom chosen from oxygen, nitrogen and sulfur and optionally substituted by at least one member of the group consisting of halogen, hydroxyl, cyano, trifluoromethyl, nitro, alkyl, alkenyl, alkoxy and acyl of up to 6 carbon atoms, free, salified or esterified carboxy, tetrazolyl or oxazolyl, or $R_{13}$ and $R_{14}$ or $R_{15}$ and $R_{16}$ form respectively with the nitrogen atom to which they are attached a monocyclic of 5 or 6 ring members or condensed rings of 8 to 10 ring members optionally containing at least one heteroatom chosen from oxygen, nitrogen and sulfur and optionally substituted by at least one member of the group consisting of halogen, hydroxyl, cyano, trifluoromethyl, nitro, alkyl, alkenyl, alkoxy and acyl of up to 6 carbon atoms, free, salified or esterified carboxy, tetrazolyl or oxazolyl, or $R_{15}$ and $R_{16}$ individually are acyl of a carboxylic acid of 1 to 6 carbon atoms, the said products of formula I being in all possible racemic, enantiomeric and diastereoisomeric isomer forms, as well as the addition salts with mineral or orgnic acids or with mineral or organic bases of said products of formula I. In the products of formula I, halogen is preferably chlorine, but can also be fluorine, bromine or iodine and acyl is preferably decanoyl, dodecanoyl and more preferably acetyl, propionyl, butyryl or benzoyl, but can also be hexanoyl, acryloyl, crotonoyl or carbamoyl or formyl.

Esterfied carboxy preferably is lower alkoxycarbonyl such as methoxycarbonyl, ethoxycarbonyl, tert-butoxycarbonyl or benzyloxycarbonyl, but also can be an aryloxycarbonyl such as phenoxycarbonyl, halophenoxycarbonyl such as chlorophenoxycarbonyl or aralkyloxycarbonyl such as benzoylcarbonyl or phenylacetylcarbonyl, Cycloalkyl may be cyclopropyl, cyclobutyl, cyclopentyl or cyclohexyl.

Alkyl is preferably methyl, ethyl, n-propyl, isopropyl, n-butyl, isobutyl, sec-butyl and tert-butyl but can also be pentyl or hexyl and particularly isopentyl and isohexyl. Alkenyl is preferably vinyl, allyl, 1-propenyl, butenyl and particularly buten-1-yl or pentenyl. Alkynyl is preferably ethynyl, propargyl, butynyl or pentynyl.

Alkoxy is preferably methoxy, ethoxy, propoxy, isopropoxy, linear, secondary or tertiary butoxy, but can also be pentyloxy and hexyloxy. Alkylthio can have the alkyl indicated above for alkyl such as methylthio, ethylthio, propylthio, isopropylthio, n-butylthio, sec-butylthio, tert-butylthio and also isopentylthio or isohexylthio.

Alkylene is preferably methylene and ethylene but also can be n-propylene, isopropylene, n-butylene, isobutylene, sec-butylene and tert-butylene. The alkylene can be also substituted for example by alkyl optionally substituted by an amino acid chosen from the 20 natural amino acids such as glycine, alanine, leucine, isoleucine, valine or phenylalanine.

Aryl includes carbocyclic or heterocyclic monocyclic or condensed rings, it being understood that the heterocyclics can contain one or more identical or different heteroatoms chosen from oxygen, nitrogen or sulfur. Monocyclics preferably includes 5 or 6 ring members such as carbocyclic monocyclic like phenyl. Among the heterocyclic monocyclics are thienyl, furyl, pyrannyl, pyrrolyl, imidazolyl, pyrazolyl, pyridyl, pyrazinyl, pyrimidinyl, pyridazinyl, thiazolyl, thiadiazolyl, oxazolyl, furazannyl, pyrrolinyl such as delta 2-pyrrolinyl, imidazolinyl such as delta 2-imidazolinyl, pyrazolinyl such as delta 3-pyrazolinyl as well as position isomers of the heteroatom or heteroatoms which these can contain such as isothiazolyl or isoxazolyl.

The condensed rings preferably contain 8 to 14 ring members such as carbocyclic condensed rings, naphthyl and phenanthryl or indane and indenyl. Among the heterocyclic condensed rings are benzothienyl, naphtho(2,3-b)thienyl, thiaanthrenyl, isobenzofurannyl, chromenyl, xanthenyl, phenoxathiinyl, indolizinyl, isoindolyl, 3H-indolyl, indolyl, indazolyl, purinyl, quinolizinyl, isoquinolyl, quinolyl, phthalazinyl, naphthyridinyl, quinoxalinyl, quinazolinyl, cinnolinyl, pteridinyl, carbazolyl, betacarbolinyl, acridinyl, phenazinyl, phenothiazinyl, phenoxazinyl, indolinyl, isoindolinyl or also condensed polycyclic systems of heterocyclic monocyclics as defined above such as furo(2,3-b)pyrrole or thieno (2,3-b)furan.

Examples of such aryls are phenyl, naphthyl, thienyl such as thien-2-yl and thien-3-yl, furyl such as fur-2-yl, pyridyl such as pyrid-3-yl, pyrimidyl, pyrrolyl, thiazolyl, isothiazolyl, diazolyl, triazolyl, tetrazolyl, thiadiazolyl, thiatriazolyl, oxazolyl, oxadiazolyl, 3- or 4-isoxazolyl; condensed heterocyclics containing at least one heteroatom chosen from sulfur, nitrogen and oxygen such as benzothienyl such as benzothien-3-yl, benzofuryl, benzopyrrolyl, benzimidazolyl, benzoxazolyl, thionaphthyl, indolyl or purinyl. Such aryl radicals can be optionally substituted such as N-substituted pyrrolyl like N-methylpyrrolyl, substituted 3- or 4-isoxazolyl, for example, 3-aryl-5-methylisoxazol-4-yl, the aryl group being phenyl or halophenyl.

Arylalkyl and arylalkenyl in which respectively the alkyl, alkenyl and aryl can have the values defined above for these groups. Examples of such arylalkyl are benzyl, diphenylmethyl, triphenylmethyl, naphthylmethyl, indenylmethyl, thienylmethyl such as thien-2-ylmethyl, furylmethyl such as furfuryl, pyridinylmethyl, pyrimidylmethyl or pyrrolylmethyl, it being understood that in the non-exhaustive list of examples mentioned above, alkyl can equally be ethyl, propyl or butyl such as phenethyl. Examples of arylalkenyl are given above for arylalkyl in which the alkyl is replaced by alkenyl such as phenylvinyl or phenylallyl, it being understood that the phenyl can equally be replaced by naphthyl, pyridyl or by one of the aryls as defined above in the non-exhaustive list of aralkyl.

Aryloxy and arylthio may have the aryl values defined above. In a non-exhaustive manner are examples of such aryloxy and arylthio such as phenoxy, naphthyloxy, pyridyloxy, phenylthio and naphthylthio.

In the products of formula I, monocyclic and condensed rings are aryls either unsaturated carbocyclics or heterocyclics defined above but also saturated heterocyclics. The heterocyclics as defined above can contain one or more different or identical heteroatoms chosen from oxygen, nitrogen or sulfur. Among the saturated heterocyclic monocyclics are pyrrolidinyl, imidazolidinyl, pyrazolidinyl, piperidyl, piperazinyl, morpholinyl, thiomorpholinyl or azepinyl. Among the saturated heterocyclics of condensed rings are 1-oxa spiro(4,5)decyl, tetrahydropyran-2-spirocyclohexyl, cyclohexanespiro-2'-tetrahydrofuran or 1,10-diazaanthr- 4-yl.

In the products of formula I, carbamoyl means in addition to carbamoyl also carbamoyls substituted by one or two members chosen from alkyl, alkenyl, arylalkyl and aryl as defined above and optionally substituted as defined above. Amino can be in addition to amino, also substituted aminos such as the values defined above for the carbamoyl.

The carbamoyls and aminos can carry one or more of the substituents defined in the products of formula I and may be

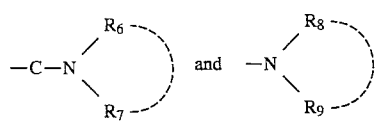

as defined above, in which two identical or different radicals are linked to the nitrogen atom which can take the values indicated above for these groups and carry the optional substituents defined for these groups. Examples include hydrogen to give amino and carbamoyl, alkyl as defined above to give substituted amino or carbamoyl such as monoalkyl- or dialkylamino or N-monoalkyl- or dialkylcarbamoyl in which the alkyl can have the values indicated above and optionally substituted as indicated above.

For example, in a non-exhaustive manner, alkyl may be such as methyl, ethyl, isopropyl, trifluoromethyl, pentafluoromethyl, hydroxymethyl, hydroxyethyl, methoxymethyl, methoxyethyl and ethoxyethyl and alkenyl defined above such as vinyl and allyl. Aryl or arylalkyl may be as defined above such as carbocyclic or heterocyclic and particularly phenyl, benzyl, phenethyl, naphtyl, indolyl, indolinyl, thienyl, furyl, pyrrolyl, pyridyl, pyrolidinyl, piperidino, morpholino, piperazinyl optionally substituted by at least one substituent above such as methylpiperazinyl, fluoromethylpiperazinyl, ethylpiperazinyl, propylpiperazinyl, phenylpiperazinyl or benzylpiperazinyl.

In a non-exhaustive manner, lower N-monoalkylcarbamoyl may be such as N-methylcarbamoyl, N-ethylcarbamoyl; lower N-N-dialkylcarbamoyl such as N-N-dimethylcarbamoyl, N-N-diethylcarbamoyl; N-phenylcarbamoyl; N-benzylcarbamoyl; N-hydroxyalkylcarbamoyl or N-hydroxyarylcarbamoyl such as N-hydroxymethylcarbamoyl; N-hydroxyphenylcarbamoyl; N-haloalkylcarbamoyl or N-haloarylcarbamoyl such as N-chloromethylcarbamoyl, N-dichlorophenylcarbamoyl, N-trifluoromethylcarbamoyl or N-trifluoromethylphenylcarbamoyl.

When $R_6$ and $R_7$ on the one hand or $R_8$ and $R_9$ on the other hand form together with the nitrogen atom to which they are attached a heterocycle, examples are pyrrolyl, imidazolyl, pyridyl, pyrazinyl, pyrimidyl, indolyl, indolinyl, purinyl, quinolyl, pyrrolidinyl, piperidyl, piperidino, morpholino and piperazinyl optionally substituted by the substituents already mentioned previously and particularly by one or more of chlorine and fluorine, methyl, ethyl, isopropyl, tert-butyl, methoxy, ethoxy, propoxy, benzoyl, methoxycarbonyl, ethoxycarbonyl, as methylpiperazinyl, ethylpiperazinyl, propylpiperazinyl, phenylpiperazinyl or benzylpiperazinyl. In the last two groups, the phenyl and benzyl can be substituted as indicated previously for the aryl, arylalkyl and arylalkenyl.

Acyl of $R_8$ and $R_9$ are as defined previously and can be chosen from acetyl, propionyl, butyryl, valeryl or carbamoyl. $Y_1$ and $Y_2$ can be the values defined above for the monocyclic aryl or condensed rings, it being understood that in the case where B is a single bond, $Y_2$ can also be non-cyclized such as hydrogen, cyano or free, salified or esterified carboxy, the esterified carboxyl preferably being lower alkoxycarbonyl such as methoxycarbonyl, ethoxycarbonyl or benzyloxycarbonyl. $Y_1$ or $Y_2$ can individually be aryl optionally substituted by one or more groups chosen, preferably, from halogen, hydroxyl, nitro, alkyl, alkenyl, alkoxy, acyl and free, salified or esterified carboxy of up to 6 carbon atoms and being as defined above.

The addition salts with the mineral or organic acids of the products of formula I can be, for example, the salts formed with the following acids: hydrochloric acid, hydrobromic acid, hydroiodic acid, nitric acid, sulfuric acid, phosphoric acid, propionic acid, acetic acid, formic acid, benzoic acid, maleic acid, fumaric acid, succinic acid, tartaric acid, citric acid, oxalic acid, glyoxylic acid, aspartic acid, ascorbic acid, alkylmono-sulfonic acids such as methanesulfonic acid, ethanesulfonic acid, propanesulfonic acid, alkyldisulfonic acids such as methanedisulfonic acid, alpha, beta-ethanedisulfonic acid, arylmonosulfonic acids such as benzenesulfonic acid and aryldisulfonic acids.

The carboxy of the products of formula I can be salified by mineral bases such as an equivalent of sodium, potassium, lithium, calcium, magnesium or ammonium or by organic bases such as methylamine, propylamine, trimethylamine, diethylamine, triethylamine, N,N-dimethylethanolamine, tris (hydroxymethyl) amino methane, ethanolamine, pyridine, picoline, dicyclohexylamine, morpholine, benzylamine, procaine, lysine, arginine, histidine, N-methylglucamine.

The alkyl, alkenyl and alkynyl as defined above as well as the alkyl or alkenyl of alkylthio, arylalkyl and arylalkenyl as defined above can be not substituted or carry one or more substituents chosen from the group formed by halogens such as chloro or bromo, as in, for example, 2-bromoethyl; hydroxyl; aryl as defined above being a monocyclic or condensed rings carbocyclic or heterocyclic, it being understood that heterocyclics as defined above can contain one or more heteroatoms chosen from oxygen, nitrogen or sulfur and that when these heterocyclics contain more than one heteroatom, the heteroatoms of these heterocyclics can be identical or different, this heterocyclic radical being able to be linked by a carbon atom or, if need be, by a nitrogen. Arylalkyl in which the aryl is as defined above; cycloalkyl, for example cyclopropyl, cyclopentyl or cyclohexyl; cycloalkenyl such as cyclohexenyl can be optionally substituted such as 1,3-dimethyl cyclohexene; alkoxy, such as methoxy, ethoxy, n-propoxy or iso-propoxy as in methoxymethyl or 1-ethoxyethyl; substituted alkoxy such as trihaloalkoxy such as trifluoromethoxy; aryloxy, for example phenoxy; aralkoxy, for example benzyloxy; mercapto; alkylthio, for example methylthio or ethylthio; substituted alkylthio such as trihaloalkylthio such as trifluoromethylthio; arylthio; aralkylthio; amino as 2-aminoethyl; amino substituted by one or two groups of alkyl, alkenyl, aryl and arylalkyl as defined above such as monoalkylamino i.e. methylamino or ethylamino, such as dialkylamino i.e. dimethylamino; nitro, cyano; azido; carboxy; esterified carboxy, for example methoxycarbonyl or ethoxycarbonyl; formyl; acyl, for example acetyl, propionyl or benzoyl; acyl substituted for example by amino as defined above or by cyclic linked to an acyl by a nitrogen atom, this cyclic being able to optionally contain one or more heteroatoms chosen from nitrogen, oxygen or sulfur and as defined above; acyloxy, for example acetoxy or propionyloxy; carbamoyl; substituted carbamoyl for example a lower N-monoalkylcarbamoyl such as N-methylcarbamoyl, N-ethylcarbamoyl, a lower N,N-dialkylcarbamoyl such as N,N-dimethylcarbamoyl, N,N-diethylcarbamoyl; an N-(lower hydroxyalkyl) carbamoyl such as N-(hydroxymethyl) carbamoyl, N-(hydroxyethyl) carbamoyl, a lower carbamoylalkyl such as carbamoylmethyl, carbamoylethyl; phthalimido; acylamido, for example acetamido or benzamido; alkoxycarbonylamino, for example methoxycarbonylamino or ethoxycarbonylamino; or aralkoxycarbonylamino, for example benzyloxycarbonylamino.

The aryl and aryloxy as defined above and the aryl of arylalkyl and arylalkenyl as defined above can be not substituted or carry one or more substituents chosen from the list indicated above for the optional substituents of alkyl, alkenyl and alkynyl as defined above, such as o-chlorophenyl but can also be substituted by one or more members chosen from the group formed by alkyl such as lower alkyl, for example methyl, ethyl or isopropyl or tertbutyl; substituted alkyl such as trihaloalkyl as in trifluoromethyl; alkenyl such as vinyl or allyl; alkynyl such as propargyl.

Among the preferred compounds of formula I as defined above are those in which the substituents that can be carried by:

a) the alkyl, alkenyl, alkynyl, alkoxy, alkylthio and cycloalkyl of $R_1$, $R_2$ and $R_3$, alkylene, alkyl, alkoxy or alkylthio of $R_{10}$ and $R_{11}$, b) the aryl, arylalkyl, arylalkenyl, aryloxy and arylthio of $R_1$, $R_2$ and $R_3$, c) the alkyl or aryl of $R_{12}$ are chosen from the group formed by halogen, hydroxyl, cyano, nitro, formyl, acyl or acyloxy of 1 to 6 carbon atoms, benzoyl, carboxy free, salified or esterified by alkyl of 1 to 6 carbon atoms, alkyl and alkenyl of up to 6 carbon atoms optionally substituted by one or more substituents chosen from halogen, hydroxyl and alkoxy of 1 to 6 carbon atoms, alkoxy and alkylthio of 1 to 6 carbon atoms, aryl and arylalkyl with alkyl of 1 to 6 carbon atoms and monocyclic of 5 or 6 ring members or condensed rings of 8 to 10 ring members optionally containing one or more heteroatoms chosen from oxygen, nitrogen and sulfur and optionally substituted by at least one member of the group consisting of halogen, hydroxyl, cyano, trifluoromethyl, nitro, alkyl, alkenyl, alkoxy and acyl of up to 6 carbon atoms, free, salified or esterified carboxy, tetrazolyl or oxazolyl,

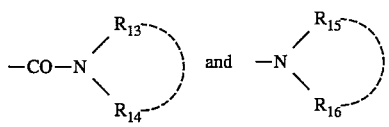

in which either $R_{13}$ and $R_{14}$ or $R_{15}$ and $R_{16}$ are individually hydrogen, alkyl or alkenyl of up to 6 carbon atoms and optionally substituted by at least one halogen or hydroxyl, alkyl or alkenyl of 2 to 6 carbon atoms substituted by alkoxy of 1 to 6 carbon atoms, aryl or arylalkyl with alkyl of 1 to 6 carbon atoms and the aryl is a monocyclic of 5 or 6 ring members or condensed rings of 8 to 10 ring members optionally containing at least one heteroatom chosen from oxygen, nitrogen and sulfur and optionally substiuted by at least one member of the group consisting of halogen, hydroxyl, cyano, trifluoromethyl, nitro, alkyl, alkenyl, alkoxy and acyl of up to 6 carbon atoms, free, salified or esterified carboxy, tetrazolyl or oxazolyl or $R_{13}$ and $R_{14}$ or $R_{15}$ and $R_{16}$ form respectively with the nitrogen atom to which they are attached a monocyclic of 5 or 6 ring members or condensed rings of 8 to 10 ring members optionally containing one or more heteroatoms chosen from oxygen, nitrogen and sulfur and optionally substituted by at least one member of the group consisting of halogen, hydroxyl, cyano, trifluoromethyl, nitro; alkyl, alkenyl, alkoxy and acyl of up to 6 carbon atoms, free, salified or esterified carboxy, tetrazolyl or oxazolyl, or $R_{15}$ and $R_{16}$ individually are acyl of a carboxylic acid of 1 to 6 carbon atoms.

Said products of formula I being in all possible, racemic enantiomeric and diastereoisomeric isomer forms, as well as the addition salts with mineral or organic acids or with mineral or organic bases of said products of formula I, The

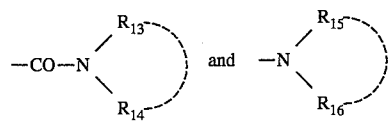

as defined above can have the same values as those defined for

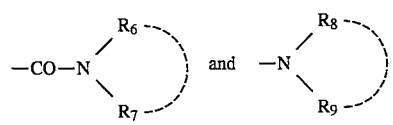

Among the substituents that can be contained by the alkyl, alkenyl, alkynyl, alkoxy, alkylthio, aryl, aryloxy, arylthio, arylalkyl and arylalkenyl as defined above are more particularly halogen atoms such as chloro and bromo; hydroxyl; acyl such as acetyl, propionyl, butyryl, valeryl, hexanoyl, acryloyl, crotonoyl or carbamoyl; benzoyl; esterified carboxy preferably being a lower alkoxy carbonyl such as methoxycarbonyl, ethoxycarbonyl or benzyloxycarbonyl; alkyl such as methyl or ethyl; amino; substituted amino such as monoalkyl- and dialkylamino, for example methylamino, ethylamino or dimethylamino; alkoxy, for example methoxy, ethoxy or isopropoxy; aryl such as phenyl, biphenyl, naphthyl, indenyl, indolyl or indolinyl; aralkyl such as benzyl or phenethyl; alkyl, alkoxy and aryl as defined above optionally substituted by one or more chosen, for example, from the group of hydroxy, alkyl and alkoxy, for example methyl, ethyl, tert-butyl, methoxy, ethoxy, isopropoxy; substituted amino such as monoalkyl- and dialkylamino, for example methylamino, ethylamino or dimethylamino; carbocyclic or heterocyclic monocyclics of 6 ring members such as phenyl, pyrannyl, pyridyl, pyrimidinyl, pyridazinyl, pyrazinyl, piperidyl, piperazinyl, piperidino and morpholino; carbocyclic or heterocyclic of monocyclics of 5 ring members such as furyl, pyrrolyl, pyrrolinyl, imidazolyl or pyrazolyl, isothiazolyl, isoxazolyl, pyrrolidinyl, imidazolidinyl, pyrazolidinyl; carbocyclic or heterocyclic condensed rings such as naphthyl, indolyl, quinolyl or purinyl as well as their position isomers of the heteroatom or heteroatoms for example nitrogen such as indazolyl or isoquinolyl.

When such heterocyclics contain one or more nitrogen atoms, the nitrogen atom(s) may be substituted for example, by alkyl or alkoxy of 1 to 5 carbon atoms as defined above, for example methyl, ethyl, isopropyl, tert-butyl, methoxy or ethoxy, phenyl or benzyl all optionally substituted by the substituents already mentioned above for aryl and arylalkyl. Examples include methylpiperazinyl, ethylpiperazinyl, propylpiperazinyl, phenylpiperazinyl or benzylpiperazinyl.

Among the particularly preferred values of such groups are phenyl, naphthyl, pyridyl, piperazinyl, pyrimidinyl, pyridazinyl and pyrazinyl.

A preferred group of the products of formula I are those of the formula

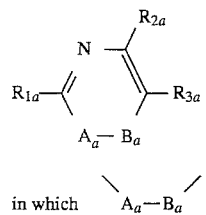

Ia is either a group:

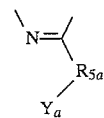

or: 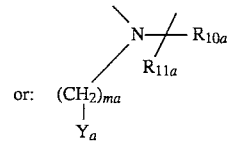

wherein $R_{5a}$ is a single bond, —NH—, —O(CH$_2$)$_m$—, —S(CH$_2$)$_m$—, m is an integer from 0 to 4 or methylene or ethylene, $m_a$ is an integer from 0 to 2, $Y_a$ is phenyl or biphenyl optionally substituted by at least one member of the group consisting of hydroxyl; halogen; alkyl and alkoxy of up to 4 carbon atoms; trifluoromethyl; cyano; nitro; amino; carbamoyl; free, salified or esterified carboxy; tetrazolyl; isoxazolyl; phenoxy; benzyl; —(CH$_2$)$_{p1}$—SO$_2$—X$_1$—R$_{17}$ in which $p_1$ is 0, 1 or 2, —X$_1$— is a single bond or —NH—, —NH—CO— and —NH—CO—NH— and $R_{17}$ is selected from the group consisting of methyl, ethyl, vinyl, allyl, pyridylmethyl, pyridylethyl, pyridyl, n-propyl, phenyl, pyrimidyl, 2-tetrazolyl, 2-thiazolyl, benzyl, 2-methyltetrahydrofuranyl, 2-(4-nitro)-pyridyl, diazolyl, ethylpiperidinyl, 2-(4-methyl)-thiazolyl, amino or carbamoyl substituted by one or two chosen from —(CH$_2$)$_{p1}$SO$_2$—X$_1$—R$_{17}$ as defined above, alkyl and alkenyl of up to 4 carbon atoms, all optionally substituted by at least one halogen, hydroxyl, alkyl and alkoxy of 1 to 4 carbon atoms, trifluoromethyl, cyano, free, salified or esterified carboxy or tetrazolyl; $R_{10a}$ and $R_{11a}$ together form an oxo or methylene or individually are hydrogen, halogen, hydroxyl or alkoxy of 1 to 4 carbon atoms, $R_{1a}$ is alkyl, alkenyl, alkynyl, alkylthio of up to 10 carbon atoms, or cycloalkyl of 3 to 7 carbon atoms, all optionally substituted by at least one member of the group consisting of halogen, hydroxyl, alkoxy of 1 to 6 carbon atoms, alkylthio, acyl, free, salified or esterified carboxy, formyl cyano, nitro, amino optionally substituted by one or two alkyl of 1 to 6 carbon atoms, cycloalkyl of 3 to 7 carbon atoms and aryl optionally substituted by at least one member of the group consisting of halogen, hydroxyl, alkyl, alkenyl and alkoxy containing at most 6 carbon atoms, haloalkyl, alkylthio, haloalkylthio, haloalkoxy, aryloxy, arylalkoxy, carbamoyl, acyl, acyloxy, free, salified or esterified carboxy, tetrazolyl, cyano, nitro, amino optionally substituted by one or two alkyl of 1 to 6 carbon atoms and phenyl optionally substituted by at least one member of the group consisting of halogen, hydroxyl, alkyl and alkoxy of 1 to 4 carbon atoms, trifluoromethyl, free, salified or esterified carboxy and tetrazolyl, $R_{2a}$ and $R_{3a}$ individually are selected from the group consisting of hydrogen, halogen, hydroxyl, mercapto, cyano, nitro, formyl, benzoyl, an acyl of 1 to 6 carbon atoms, carboxy, free, salified or esterified by alkyl of 1 to 4 carbon atoms, alkyl, alkenyl, alkoxy and alkylthio of up to 10 carbon atoms, phenyl, phenoxy, naphthyl, benzyl, phenylthio, biphenyl, indole, all optionally substituted by at least one member of the group consisting of halogen, hydroxyl, alkoxy of 1 to 4 carbon atoms, trifluoromethyl, cyano, acyl, formyl, free, salified or esterified carboxy, tetrazolyl, isoxazolyl and pyridyl, amino, mono- or dialkylamino, carbamoyl, pyrrolyl, morpholino, piperazinyl, pyrrolylmethyl, morpholinomethyl, piperazinylmethyl, pyrrolylcarbonyl, morpholinylcarbonyl, piperazinylcarbonyl, all the piperazinyls being optionally substituted on the second nitrogen atom by alkyl or phenyl optionally substituted by at least one member of the group consisting of halogen, hydroxyl, nitro, alkyl, alkoxy or acyl containing at most 4 carbon atoms, trifluoromethyl, cyano, free, salified or esterified carboxy, tetrazolyl and isoxazolyl.

When at least one of $R_{2a}$ and $R_{3a}$ is alkenyl it can be preferably

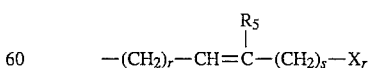

in which r and s are individually an integer from 0 to 6 with the sum of r+s being less than or equal to 8, $X_r$ is hydrogen or a free, esterified or salified carboxy, formyl or hydroxy.

Preferably, s is not equal to 0 and $R_5$ is hydrogen or alkyl.

More particularly, the products of formula I are those hereafter called $I_b$ in which: m is 0 or 1, $R_5$ is —CH$_2$—, —NH—, —O— or —OCH$_2$—, Y is phenyl or biphenyl optionally substituted by at least one member chosen from cyano, free, salified and esterified carboxy, tetrazolyl and —(CH$_2$)$_p$—SO$_2$—X$_p$—R$_{12p}$ in which p is 0 or 1, —X$_p$— is a single bond or —NH—, —NH—CO— and —NH—CO—NH— and R$_{12p}$ is methyl, phenyl or benzyl optionally substituted by at least one member chosen from halogen, hydroxyl, trifluoromethyl, cyano, free, salified or esterified carboxy or tetrazolyl, R$_{10}$ and R$_{11}$ together form an oxo or methylene, R$_1$ is ethyl, propyl, isopropyl, propen-1-yl, butyl or buten-1-yl, R$_2$ and R$_3$ are individually selected from the group consisting of hydrogen, halogen, hydroxyl, formyl, free, salified or esterified carboxy, alkyl, alkenyl, alkoxy and alkylthio of up to 6 carbon atoms and optionally substituted by at least one member of the group consisting of halogen, hydroxyl, cyano, free, salified or esterified carboxy, formyl, pyridyl, phenyl and biphenyl, the phenyl and biphenyl optionally substituted by at least one member of the group consisting of halogen, hydroxyl, cyano, carboxy free, salified or esterified by alkyl of 1 to 4 carbon atoms, alkoxy and alkyl of 1 to 4 carbon atoms, trifluoromethyl, amino, mono- or dialkylamino, tetrazolyl and isoxazolyl.

More preferred products of formula I are those called I$_C$ in which: m is 1, R$_5$ is —CH$_2$—, Y is phenyl or biphenyl optionally substituted by at least one cyano, free, salified and esterified carboxy and tetrazolyl, R$_{10}$ and R$_{11}$ together form oxo, R$_1$ is n-butyl, R$_2$ and R$_3$ are chosen from the group consisting of halogen, hydroxyl, alkoxy and alkyl optionally substituted by cyano, free, salified or esterified carboxy, phenyl and biphenyl optionally substituted by cyano, carboxy free, salified or esterified by alkyl of 1 to 4 carbon atoms or tetrazolyl.

Among the products which are a subject of the invention is preferred 2-butyl-4-[(2'-carboxy-(1,1'-biphenyl)-4-yl)-methyl]-6-chloro- 5-pyrimidineacetic acid.

The novel process of the invention for the preparation of the compounds of formula I comprises reacting a compound of the formula

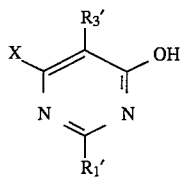
II in which R$_1$' and R$_3$' have the above meanings for R$_1$ and R$_3$ in which the optional reactive functions are optionally protected and X is hydroxyl or R$_2$' which has the above meaning for R$_2$ in which the optional reactive functions are optionally protected either with a compound of the formula

Hal—(CH$_2$)$_m$—Y'   III in which Hal is halogen, m has the meaning indicated above and Y' had the meaning for Y in which the optional reactive functions are optionally protected to obtain a product of the formula

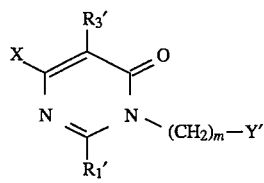
IV in which R$_1$', R$_3$', X, m and Y' have the above meanings or with a halogenating agent to obtain a product of the formula

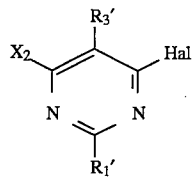
V in which R$_1$' and R$_3$' have the above meanings, Hal is halogen and X$_2$ is Hal or R$_2$' as defined above, and reacting the latter: either when X$_2$ is halogen with an excess of a compound of the formula

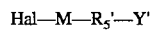
Hal—M—R$_5$'—Y'   VI in which Hal and Y' have the above meanings, M is zinc or copper and R$_5$' has the above meaning for R$_5$ in which the optional reactive function are optionally protected to obtain a product of the formula

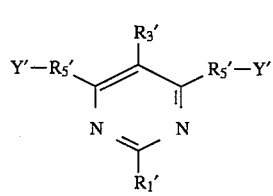
VIII in which R$_1$', R$_3$', R$_5$' and Y' have the above meanings or with an equivalent of a compound of formula VI to obtain a compound of the formula

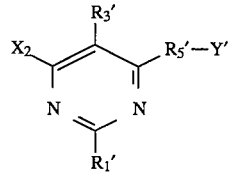
VII in which R$_1$', R$_3$', m R$_5$', X$_2$ and Y' have the above meanings and optionally reacting the compound of formula VII in which X$_2$ is halogen either with a compound of formula VI to obtain a compound of formula VIII as defined above, or with a compound of the formula

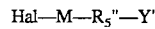
Hal—M—R$_5$"—Y'   VI' in which Hal, M and Y' have the above meanings and R$_5$", indentical to or different from R$_5$', has the meaning indicated above for R$_5$ in which the optional reactive functions are optionally protected to obtain a product of the formula

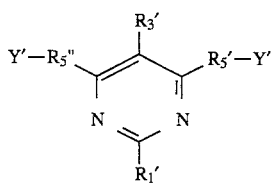

IX in which $R_1'$, $R_3'$, $R_5'$, $R_5''$ and Y' have the above meanings which products of formula IV, VII, VIII and IX either represent products of formula I to obtain other products of formula I or can be optionally subjected to one or more of the following reactions in any order:

a reduction of oxo into hydroxyl, a reduction of hydroxyl or of oxo tautomer form into methine, a conversion of the oxo into alkylene, a substitution reaction of hydroxyl by halogen, an alkylation of hydroxyl into alkoxy, a substitution reaction of halogen by a compound of formula Z'—M—Hal in which Z' can have the above meanings for $R_1$, $R_2$ or $R_3$ in which the optional reactive functions are optionally protected by protective groups, M is a metal chosen from magnesium, copper and zinc and Hal is halogen such as bromine or chlorine, a substitution reaction of hydroxyl by a compound of formula Z'—Hal in which Hal is halogen and Z' has the above meanings, a conversion reaction of oxo (=O) into thioxo (=S), an esterification of an acid function, a saponification of an ester into an acid, a conversion of alkoxy into hydroxyl, a conversion of cyano into an acid, a reduction of the carboxy into an alcohol, an oxidation of an alcohol into an aldehyde or acid, a conversion of nitrile into tetrazolyl, an elimination of the protective groups which can be carried by the protected reactive functions, a salification by an acid or by a base to obtain the corresponding salt, a resolution reaction of racemic forms into resolved products, the said products of formula I thus obtained being in all possible racemic, enantiomeric and diastereoisomeric isomer forms.

In the preferred conditions for the process of the invention, the addition reaction of the compound of formula III on the compound of formula II can be carried out by the usual methods known to one skilled in the art such as in the presence of sodium or potassium carbonate in a solvent such as dimethylformamide. In the compound of formula III, the halogen is preferably bromine but can also be chlorine or iodine.

The halogenation of the compound of formula II to obtain the product of formula V can be carried out by the usual methods such as in the presence of phosphorus oxychloride or phosphorus pentachloride in a solvent such as toluene or in the optional presence of N,N-diethylaniline.

The addition reaction of the compound of formula VI in the form of an organometal on the halogenated derivative of formula V to obtain the product of formula VII can be carried out by the usual methods. The preliminary preparation of the organometal is carried out by the usual methods such as by reaction of the corresponding halogenated derivative in which the halogen is for example bromine or chlorine in the presence of the corresponding metal such as zinc or magnesium or copper in a solvent such as tetrahydrofuran, ether or dimethoxymethane at a temperature of 0° to 5° C.

The reaction of the organometal of formula VI with the halogenated derivative of formula V can be carried out in the presence of a catalytic quantity of a transition metal complex such as palladium or nickel in a solvent such as tetrahydrofuran, toluene or dimethylformamide at a temperature of approximately 50° C. When the compound of formula VI is used in excess relative to the compound of formula V, the compound of formula VIII can be obtained under the same reaction conditions.

The addition reaction of the compound of formula VI on the compound of formula VII to obtain the product of formula VIII or the addition reaction of the compound of formula VI' on the compound of formula VII to obtain the product of formula IX can be carried out by the usual methods and especially under the same conditions as indicated above for the addition reaction of the compound of formula VI on the compound of formula V to obtain the product of formula VII.

The products of formulae IV, VII, VIII and IX cannot constitute the products of formula I or constitute the products of formula I in which the optional reactive functions are optionally protected and are optionally subjected to one or more of the reactions indicated above to give the products of formula I. The reactions indicated above can be carried out by the usual methods such as under the conditions indicated hereafter.

The reduction of the oxo into hydroxyl can be carried out for example by catalytic hydrogenation such as by platinum or nickel. The reduction of hydroxyl or oxo tautomer form into methine can be carried out using a reducing agent such as lithium aluminium hydride or by catalytic reduction on palladium in the presence of hydrogen. The conversion of oxo into alkylene can be carried out by methylene triphenylphosphorane in a solvent such as tetrahydrofuran.

The substitution of hydroxyl by halogen can be carried out by treatment with a chlorinating agent such as phosphorous pentachloride or phosphorous oxychloride optionally in a solvent such as dioxane or tetrahydrofuran. The substitution of hydroxyl by Z' as defined above can be carried out by a preliminary substitution reaction of hydroxyl by halogen carried out as indicated above. The substitution of Z' as defined above on halogen can be carried out by reaction with an organometal such as an organozinc of formula Z—Zn—Br, carried out under the conditions described above for the reaction of the organometal of formula VI with the halogenated derivative of formula V.

The conversion of the oxo into thioxo can be carried out by the usual methods such as using a Lawesson reagent or phosphorous pentasulfide at reflux in a solvent such as toluene or an alcohol such as ethanol.

The products described above can, if desired, be the subject, on the optional carboxy functions, of esterification reactions that can be carried out by the usual methods. The optional esters, of the products described above can be saponified into an acid by the usual conditions, notably by acid hydrolysis with hydrochloric or sulfuric acid or alkaline hydrolysis with sodium hydroxide or potassium hydroxide in the alcoholic medium such as in methanol.

The optional alkoxy such as methoxy of the products described above can be, if desired, converted into hydroxyl or alcohol by usual conditions for example by boron tribromide in a solvent such as methylene chloride, by pyridine hydrobromate or hydrochlorate or also by hydrochloric acid or hydrobromic acid in water or acetic acid at reflux.

The optional cyano of the products described above can be, if desired, converted into acid by the usual conditions, for example by a hydrolysis carried out in an acid medium such as in a sulfuric acid, glacial acetic acid and water mixture, preferably in equal proportions, or also in a mixture of sodium hydroxide, ethanol and water at reflux.

The optional esterified carboxy of the products described above can, if desired, be reduced to alcohol by known methods notably by lithium aluminium hydride in a solvent such as tetrahydrofuran or dioxane or ethyl ether.

The optional carboxy of the products described above can, if desired, be reduced to alcohol by known methods such as first esterified, then converted into an alcohol as indicated above.

The oxidation of the alcohol into an aldehyde or acid can be carried out by the usual conditions. The conversion of nitrile into tetrazolyl can be carried out as indicated in European Application EP 0,253,310.

The various reactive functions that can be carried by certain reaction compounds defined above can, if necessary, be protected. For example, hydroxyl, acyl, free carboxy or amino and monoalkylamino can be protected by the appropriate protective groups. The following list, non-exhaustive, of examples of protection of reactive functions can be mentioned: hydroxyl groups can be protected by alkyl, trimethylsilyl, dihydropyran, methoxymethyl or tetrahydropyrannyl, the amino can be protected by acetyl, trityl, benzyl, tert-butoxycarbonyl, phthalimido or other groups known in the chemistry of peptides, acyl groups such as formyl can be protected in the form of cyclic or non-cyclic ketals such as dimethyl- or diethylketal or ethylene dioxyketal, acid functions of the products described above, can be, if desired, amidified by a primary or secondary amine in the presence of methylene chloride in 1-ethyl-1-(dimethylaminopropyl) carbodiimide hydrochloride at ambient temperature and the acid functions cn be protected in the form of easily cleavable esters such as benzylic or tertbutylic esters or esters known in the chemistry of the peptides.

The elimination of these protective groups is carried out under the usual conditions known to a man skilled in the art, notably by acid hydrolysis with an acid such as hydrochloric acid, benzene sulfonic acid or p-toluene sulfonic acid, formic acid or trifluoroacetic acid.

The phthalimido group is eliminated with hydrazine and a list of different protective groups which can be used will be found for example in Patent No. BF 2,499,995.

The products described above can optionally be subjected to salification reactions with an acid or with a base, particularly on the optional carboxy functions, these reactions being able to be carried out by the usual methods.

The optional optically active forms of the products of formula I can be prepared by resolution of the racemates by usual methods.

The angiotensin II inhibiting compositions of the invention are comprised of an angiotensin II inhibiting effective amount of at least one compound of formula I and its non-toxic, pharmaceutically acceptable salts and an inert pharmaceutical carrier. The compositions may be in the form of tablets, dragees, capsules, granules, ointments, creams, suppositories, gels, injectable solutions or aerosols.

Examples of suitable carriers or excipients are talc, gum arabic, lactose, starch, magnesium stearate, cocoa butter, aqueous or non-aqueous vehicles, fatty substances of animal or vegetable origin, paraffin derivatives, glycols, various wetting, dispersing or emulsifying gents, preservatives.

The compositions are endowed with antagonistic properties for the angiotensin II receptor and are thus inhibitors of the effects of angiotensin II, especially of the vasoconstrictive effect and also the trophic effect at the level of the myocytes. They can be used in the treatment of arterial hypertension, cardiac insufficiencies, renal insufficiencies and in the prevention of the post-angioplasty recurrence of stenosis. They can also be used in the treatment of glaucoma, certain gastro-intestinal, gynaecological disorders and especially for a relaxing effect at the level of the uterus.

The novel method of inhibiting angiotensin II activity in warm-blooded animals, including humans, comprises administering to warm-blooded animals an angiotensin II inhibiting amount of at least one compound of formula I and their non-toxic pharmaceutically acceptable salts. The compounds may be administered orally, rectally, parenterally or topically to the skin and mucous. The usual daily dose is 0.013 to 1.33 mg/kg depending on the condition treated, the method of administration and the specific compound.

The starting compounds of formulae II, III, VI and VI' are commercially available or are prepared by known methods. Among the examples of the preparation of compounds of formula II described in the literature are KENNER et al, J. Chem. Soc. p. 388, (1943), HENZE et al, J. Org. Chem., Vol. 17, p. 1320 (1952) and HENNART, Bull. Soc. Chim. Fr., Vol. 741 (1959). The compounds of formulae III, VI and VI' can be halogenated or organometal derivatives of aryl groups of —$(CH_2)_m$—Y or —$R_5$—Y as defined above. Such compounds can be found commercially such as benzyl bromide or— bromo p-toluic acid.

Among the examples of the preparation of compounds of formula III described in the literature are FANTA, SYNTHESIS—9—(1974); Stille Angew. Chem. Int. Ed. Engli 25—508 (1986) and TIHAMA et al, SYNTHESIS, 184, (1988). Among the examples of the preparation of compounds of formula VI or VI' described in the literature are GAUDERMAR, Bull. Soc. Chim. Fr., 974 (1962) and BERK et al, J. Org. Chem., Vol. 53, p. 5789, (1988).

One process for some of the products of formula III as defined above comprises subjecting methyl iodobenzoate to the action of iodotoluene in the presence of copper powder at a temperature of approximately 100° C. to 300° C. to obtain a product of the formula

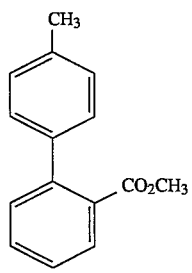

optionally hydrolyzing the esterified carboxy by standard methods such as acid or alkaline hydrolysis, which can be then subjected to a bromination reaction on the methyl by standard methods by the action of N-bromosuccinimide in carbon tetrachloride. Examples of the preparation of compounds of formula III are described in the literature such as U.S. Pat. No. 4,880,804 and European Patent No. EP 0,400, 835. Some compounds of formula VI or VI' can be prepared as indicated above for a compound of formula III by preparation of the corresponding organometal by standard methods.

In the following examples, there are described several preferred embodiments to illustrate the invention. However, it should be understood tha the invention is not intended to be limited to the specific embodiments.

EXAMPLE 1

Ethyl 2-butyl-4-chloro-6-[4-methoxycarbonyl-benzyl]-5-pyrimidine acetate

STEP A: Ethyl butanimidoate hydrochloride

Gaseous hydrochloric acid was bubbled through a solution of 20.86 ml of valeronitrile in 100 ml of ethanol for one hour at a temperature of 0° to 5° C. The mixture was kept in a sealed container for 3 days at 0° C. and after evaporation to dryness under reduced pressure, the residue in 74 ml of ether was stirred 15 minutes. After separation, 23.5 g of the expected product melting at approx. 64° C. were obtained.

STEP B: butamidine hydrochloride

Ammonia was bubbled through a solution of 23.5 g of the product of Step A in 100 ml of ethanol for 30 minutes and the mixture was stirred for 2 hours at ambient temperature followed by evaporation to dryness under reduced pressure. The product in 50 ml of ethanol was stirred for 30 minutes and after the insoluble part was filtered, the filtrate was concentrated to 25 ml and kept for 1 hour at 0° C. The insoluble part was filtered and the filtrate was evaporated to dryness to obtain 19,5 g of the expected product melting at approximately 60° C.

| NMR Spectrum: | |
|---|---|
| 0.89 | butyl $CH_3$ |
| 0.90 to 1.83 | central $CH_2$ of the butyl |
| 2.25 to 2.50 | the other $CH_2$ of the butyl |
| 8.83 | $NH_2$ |

STEP C: Triethyl 1,1,2-ethanetricarboxylate 12 ml of diethyl malonate were introduced into 120 ml of ethanol and then 5.5 grams of sodium ethylate at 98% were added over 10 minutes at 0° to +5° C. The mixture was stirred for 15 minutes at 0°+5° C. and then 8.8 ml of ethyl bromoacetate were added over 30 minutes. The mixture was stirred for 48 hours at ambient temperature and then the mixture was poured into 600 ml of water and extracted 3 times with 300 ml of methylene chloride. The organic phase was washed twice with 300 ml of water, then evaporated to dryness. The oil obtained was distilled under reduced pressure to obtain 12.4 grams of the expected product with a boiling point of 110° to 120° C. at 1.0 mm of Hg.

Analysis: $C_{11}H_{18}O_6$; molecular weight = 246.26

| Calculated: | % C 53.65 | % H 7.36 |
|---|---|---|
| Found: | 53.4 | 7.5 |

IR Spectrum in chloroform:

 1730 cm$^{-1}$, 1740 cm$^{-1}$

NMR Spectrum (CDCl$_3$) 250 MHz ppm:

| the OEt's | 1.22 to 1.32 (m) – 4.08 to 4.31 (m) |
|---|---|
|  | 3.83 (t, j=7.5) |
|  | 2.93 (d, j=7.5) |

STEP D: Ethyl 2-butyl-4,6-dihydroxy-5-pyrimidine-acetate 6.3 g of sodium ethylate at 98% were dissolved in 130 ml of ethanol, and after stirring for several minutes, 4.2 g of the product of Step B were added. The mixture was stirred for 30 minutes at ambient temperature and then 7.6 g of the product of Step C were added. The mixture was stirred for 4 days at ambient temperature, followed by evaporation to dryness under reduced pressure. The residue was dissolved in 80 ml of water, followed by washing with ethyl acetate and extracting again with 20 ml of water. The aqueous phases were combined and the pH was adjusted to approximately 5 by the addition of acetic acid. After stirring, separation, and washing with water, 3.06 g of the expected product melting at 260° C. were obtained.

| IR Spectrum in NUJOL | |
|---|---|
| C = O | 1740 cm$^{-1}$ |
| heterocycle | 1670 cm$^{-1}$ |
| | 1650 cm$^{-1}$ |
| | 1625 cm$^{-1}$ |
| | 1550 cm$^{-1}$ |

STEP E: Ethyl 2-butyl-4,6-dichloro-5-pyrimidine acetate 508 mg of the product of Step D were introduced into 5 ml of phosphorous oxychloride and the mixture was refluxed with stirring for 2 hours and evaporated to dryness under reduced pressure after several entrainments with toluene. After chromatography on silica (eluant: hexane-ethyl acetate (8/2)), 429 mg of the expected product were obtained.

Analysis: $C_{12}H_{16}N_2O_2Cl_2$; molecular weight = 291.17

| Calculated: | % C 49.50 | % H 5.53 | % Cl 24.35 | % N 9.62 |
|---|---|---|---|---|
| Found: | 50.0 | 5.7 | 23.6 | 9.1 |

IR Spectrum in chloroform:

absence of OH

 1738 cm$^{-1}$

| heteroaromatic | 1568 cm$^{-1}$ |
|---|---|
| | 1509 cm$^{-1}$ |

STEP F: Ethyl 2-butyl-4-chloro-6-[4-methoxycarbonyl-benzyl]-5-pyrimidine acetate a) [4-[methoxycarbonyl-benzyl]-zinc bromide 1 g of zinc powder was introduced into 3 ml of anhydrous tetrahydrofuran and after the mixture was cooled to 0°+5° C., a solution of 3.32 g of methyl 4-(bromomethyl)-benzoate in 15 ml of anhydrous tetrahydrofuran was introduced over one hour. The mixture was stirred at 0°+5° C. for 16 hours.

b) ethyl 2-butyl-4-chloro-6-[4-methoxycarbonyl-benzyl]-5-pyrimidine acetate.

292 mg of the product of Step E were introduced into 5 ml of tetrahydrofuran, 115 mg of tetrakis (triphenyl-phosphine)-palladium and 2.5 ml of a 0.4 M/l solution of the organozinc obtained in a) above. The mixture was stirred for 4 hours at 50° C. and then was poured into 50 ml of 0.1N hydrochloric acid. The mixture was extracted 3 times with 25 ml of ethyl acetate, washed with 25 ml of a solution saturated in sodium chloride and evaporated to dryness under reduced pressure. After chromatography on silica (eluant: hexane-methylene chloride-ethyl acetate (50/45/5)), 280 mg of the expected product melting at 78° C. were obtained.

Analysis: $C_{21}H_{25}N_2O_4Cl$; molecular weight = 404.89

| | | | | |
|---|---|---|---|---|
| Calculated: | % C 62.29 | % H 6.22 | % Cl 8.75 | % N 6.91 |
| Found: | 62.4 | 6.5 | 8.8 | 6.7 |

IR Spectrum in chloroform:

$\rangle=O$   1721 cm$^{-1}$ heterocycle   1602 cm$^{-1}$
+              1566 cm$^{-1}$
aromatic       1529 cm$^{-1}$

EXAMPLE 2

2-butyl-6-[4-carboxy-benzyl]-4-chloro-5-pyrimidine acetic acid 220 mg of the product of Example 1 were introduced into 6.6 ml of ethanol and 0.6 ml of sodium hydroxide and after stirring at ambient temperature for 3 days and followed by evaporation to dryness under reduced pressure at a temperature below 40° C., the residue was dissolved in 2 ml of water and neutralized by the addition of approximately 0.6 ml of 2N hydrochloric acid. After separating and washing with water, 160 mg of product were obtained which was crystallized from 5 ml of hot isopropanol with 5 ml of water added to it. After 24 hours at 0°+5° C., 90 mg were separated and crystallized from 9 ml of ethyl acetate at reflux. After standing at rest for 24 hours, separation took place to obtain 46 mg of the expected product melting at approx. 205° C.

Analysis: $C_{18}H_{19}N_2O_4Cl$; molecular weight = 362.82

| | | | | |
|---|---|---|---|---|
| Calculated: | % C 59.59 | % H 5.27 | % Cl 9.77 | % N 7.72 |
| Found: | 59.5 | 5.6 | 9.2 | 7.6 |

IR Spectrum in Nujol $\rangle=O$   1694 cm$^{-1}$ conjugated system   1612 cm$^{-1}$
+                    1578 cm$^{-1}$
aromatic             1562 cm$^{-1}$
                     1530 cm$^{-1}$

EXAMPLE 3

Ethyl 2-butyl-4-chloro-6-[4-[(1,1-dimethylethoxy)-carbonyl]-benzyl]-5-pyrimidine acetate a) [4-[butoxycarbonyl-benzyl]-zinc bromide Using the procedure of Example 1, 84 mg of electrolytic zinc, 0.09 ml of 1,2-dibromoethane and 2,711 g of [4-((butoxycarbonyl)-benzyl] -bromide were reacted.

b) ethyl 2-butyl-4-chloro-6-[(4-[(1,1-dimethylethoxy)-carbonyl]benzyl] 5-pyrimidine acetate.

Using the procedure of Example 1, 291 mg of the product of Step E of Example 1 were reacted with 2.91 ml of anhydrous tetrahydrofuran, 115 mg of tetrakis-(triphenylphosphine)-palladium and 2.5 ml of a solution (0.4 M/l) of orgnozinc obtained in a) above. After chromatography on silica (eluant: hexane-ethyl acetate 8/2), 200 mg of the expected product melting at approx 65° C. were obtained.

Analysis: $C_{24}H_{31}N_2O_4Cl$; molecular weight = 446.97

| | | | | |
|---|---|---|---|---|
| Calculated: | % c 64.49 | % h 6.99 | % Cl 7.93 | % N 6.26 |
| Found: | 64.5 | 7.2 | 7.5 | 6.0 |

IR Spectrum in chloroform:

$\rangle=O$   1734 cm$^{-1}$
             1708 cm$^{-1}$

Aromatic           1612 cm$^{-1}$
+                   1566 cm$^{-1}$
conjugated system   1530 cm$^{-1}$
                    1510 cm$^{-1}$

EXAMPLE 4

Ethyl 2-butyl-4-chloro-6-[(4-carboxyphenyl)-methyl]-5-pyrimidine acetate 160 mg of the product of Example 3 were introduced into 4 ml of methylene chloride and 1 ml of trifluoroacetic acid and after the mixture was stirred at ambient temperature for 2 hours 30 minutes, it was diluted with 20 ml of methylene chloride, washed twice with 10 ml of water, extracted again with 20 ml of methylene chloride and evaporated to dryness under reduced pressure to obtain 140 mg of product which was crystallized from 1 ml of methylene chloride with 3 ml of isopropyl ether added to it. After standing at rest for approximately 16 hours, separation took place to obtain 77 mg of the expected product melting at 130° C.

Analysis: $C_{20}H_{23}N_2O_4Cl$; molecular weight = 390.87

| | | | | |
|---|---|---|---|---|
| Calculated: | % C 61.45 | % H 5.93 | % Cl 9.07 | % N 7.16 |
| Found: | 61.6 | 6.1 | 9.0 | 7.0 |

IR Spectrum in chloroform:

$\rangle=O$   1734 cm$^{-1}$
             1695 cm$^{-1}$ heterocycle   1612 cm$^{-1}$
+              1576 cm$^{-1}$
aromatics      1566 cm$^{-1}$
               1529 cm$^{-1}$

EXAMPLE 5

Ethyl 2-butyl-4-chloro-6-(phenylmethyl)-5-pyrimidine acetate a) Benzylzinc bromide Using the procedure of Example 1, 2.9 g of electrolytic zinc and 4.8 ml of benzyl bromide were reacted.

b) Ethyl 2-butyl-4-chloro-6-(phenylmethyl)-5-pyrimidine acetate

Using the procedure of Example 1, 291 mg of the product of Step E of Example 1 were reacted with 2.91 ml of anhydrous tetrahydrofuran, 115 mg of tetrakis(triphenylphosphine) palladium and 1 ml of a solution (1.05 M/l) of organozinc obtained in a) above. After chromatography on silica (eluant: hexane-ethyl acetate 8/2), 230 mg of the expected product were obtained.

Analysis: $C_{19}H_{23}N_2O_2Cl$; molecular weight = 346.86

| Calculated: | % C 65.79 | % H 6.68 | % Cl 10.22 | % N 8.07 |
|---|---|---|---|---|
| Found: | 65.0 | 6.7 | 11.0 | 8.0 |

IR Spectrum in chloroform:

| >=O | 1732 cm⁻¹ |
|---|---|
| heterocycle | 1605 cm⁻¹ |
| + | 1567 cm⁻¹ |
| aromatic | 1528 cm⁻¹ |
|  | 1496 cm⁻¹ |

EXAMPLE 6

Ethyl 2-butyl-4,6-bis-(phenylmethyl)-5-pyrimidine-ethyl acetate

Using the procedure of Example 5, 2 equivalents of the product of a) of Example 5 were reacted with 291 mg of the product of Step E of Example 1 and 2.91 ml of anhydrous tetrahydrofuran, 115 mg of tetrakis(triphenylphosphine) palladium and 2 ml of a solution (1.05 M/l) of the organozinc obtained in a) of Example 5. After chromatography on silica (eluant: hexane-ethyl acetate 8/2), 360 mg of the expected product were obtained Analysis: $C_{26}H_{30}N_2O_2$; molecular weight = 402.54

| Calculated: | % C 77.57 | % H 7.51 | % N 6.59 |
|---|---|---|---|
| Found: | 77.5 | 7.6 | 6.8 |

IR Spectrum in chloroform:

| >=O | 1730 cm⁻¹ |
|---|---|
| heterocycle | 1602 cm⁻¹ |
| + | 1553 cm⁻¹ |
| aromatics | 1494 cm⁻¹ |

EXAMPLE 7

Ethyl 2-butyl-4-chloro-6-[[2'-(methoxy-carbonyl)-(1,1'-biphenyl)-4-yl]-methyl]-5-pyrimidine acetate a) [[2'-(methoxycarbonyl)-(1,1'-biphenyl)-4-yl]-methyl] zinc bromide Using the procedure of Example 1, 800 mg of electrolytic zinc, 2 ml of anhydrous tetrahydrofuran and 3.05 g of [(2'-(methoxycarbonyl)-( 1,1'-biphenyl)-4-yl)-methyl]-bromide in 12 ml of anhydrous tetrahydrofuran were reacted.
b) Ethyl 2-butyl-4-chloro-6-[(2'-(methoxycarbonyl)-(1,1'-biphenyl)- 4-yl]-methyl]-5-pyrimidine acetate Using the procedure of Example 1, 1.3 g of the product of Step E of Example 1 were reacted with 320 g of tetrakis (triphenylphospine)-palladium and 10.9 ml of the solution (0.41 M/l) obtained in a) above. After chromatography on silica (eluant: hexane-ethyl acetate 8/2), 1.47 g of the expected product were obtained.

IR Spectrum in chloroform:

| >=O | 1730 cm⁻¹ |
|---|---|
| heterocycle | 1600 cm⁻¹ |
| + | 1565 cm⁻¹ |
| aromatic | 1528 cm⁻¹ |
|  | 1480 cm⁻¹ |

EXAMPLE 8

2-butyl-4-[(2'-carboxy-(1,1'-biphenyl)-4-yl)-methyl]-6-chloro-5-pyrimidine acetic acid 175 mg of the product of Example 7 were introduced into 1.75 ml of dioxane and 1.6 ml of N sodium hydroxide and after stirring at ambient temperature for 3 days, followed by dilution with 10 ml of water, neutralization with 1.6 ml of 1N hydrochloric acid, extraction 5 times with 10 ml of methylene chloride and evaporation to dryness under reduced pressure, the residue was taken up in 2 ml of hexane, stirred for 1 hour and separated to obtain 152 mg of the expected product melting at approx 100°–110° C.

IR Spectrum in chloroform:

| >=O | 1708 cm⁻¹ |
|---|---|
| aromatic | 1600 cm⁻¹ |
| + | 1568 cm⁻¹ |
| heterocycle | 1527 cm⁻¹ |
|  | 1481 cm⁻¹ |

EXAMPLE 9

2-butyl-4-[(2'-carboxy-(1,1'-biphenyl)-4-yl)-methyl]-6-hydroxy-5-pyrimidine acetic acid 50 mg of the product of Example 7 were introduced into 1 ml of 6N hydrochloric acid and the mixture was heated to gentle reflux. The mixture was stirred for 2 hours 30 minutes and after cooling, the mixture was diluted with 2 ml of water. The pH was adjusted to 7-8 by the addition of sodium bicarbonate, then returned to pH 5-4 by the addition of acetic acid. The mixture was stirred for approximately 30 minutes, followed by separating, and rinsing with water to obtain 30 mg of the expected product melting approx. 220° C.

NMR Spectrum (DMSO) 250 MHz ppm:

| 0.87 | $CH_3$ of the butyl |
|---|---|
| 1.28 and 1.61 | the central $CH_2$'s of the butyl |
| 2.5 | the other $CH_2$ of the butyl |
| 3.45 | $CH_2$ of the carboxy |
| 3.85 | 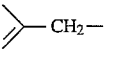 |
| 7.1 to 7.8 | the aromatics |

EXAMPLE 10

Ethyl 2-butyl-4,6-bis-[(2'-(methoxy-carbonyl)-1,1'-biphenyl]-4-yl)methyl]-5-pyrimidine acetate Using the procedure of Example 7, an excess of the product of a) of Example 7 was reacted with 1.9 g of the product of Step E of Example 1 and 3.8 ml of anhydrous tetrahydrofuran, 750 mg of tetrakis(triphenyl-phosphine) palladium and 20 ml of a solution (0.45 M/l) of organozinc obtained in a) of Example 7. After chromatography on silica (eluant: hexane-ethyl acetate 8/2), 2.22 g of the expected product were obtained.

IR Spectrum in chloroform:

| | |
|---|---|
| C = O | 1728 cm$^{-1}$ |
| heterocyclic | 1600 cm$^{-1}$ |
| + | 1555 cm$^{-1}$ |
| aromatic | 1515 cm$^{-1}$ |
| | 1481 cm$^{-1}$ |

EXAMPLE 11

2-butyl-4,6-bis-[(2'-carboxy-(1,1'-biphenyl)-4-yl)-methyl]-5-pyrimidine acetic acid 991 mg of the product of Example 10 were introduced into 6 ml of ethanol and 4.41 ml of 2N sodium hydroxide and after stirring at ambient temperature for 48 hours, followed by drying, the mixture was taken up in 20 ml of water and neutralized by the addition of 4.41 ml of 2N hydrochloric acid. Separation took place followed by washing with water, taking up in 50 ml of ethyl acetate, washing with 10 ml of water, then 10 ml of a saturated solution of sodium chloride and reextracting with 10 ml of ethyl acetate. The organic phases were concentrated and kept at 0°+5° C. for 16 hours. After separating, rinsing with ethyl acetate yielded 440 mg of the expected product melting at approx. 160° C.

Analysis: C$_{38}$H$_{34}$N$_2$O$_6$; molecular weight = 614.70

| Calculated: | % C 74.25 | % H 5.57 | % N 4.55 |
|---|---|---|---|
| Found: | 73.9 | 5.5 | 4.5 |

IR Spectrum in NUJOL

| | |
|---|---|
| \>=O | 1697 cm$^{-1}$ |
| | 1720 cm$^{-1}$ |
| Aromatic | 1641 cm$^{-1}$ |
| + | 1598 cm$^{-1}$ |
| heterocycle | 1569 cm$^{-1}$ |
| | 1552 cm$^{-1}$ |
| | 1517 cm$^{-1}$ |
| | 1480 cm$^{-1}$ |

EXAMPLE 12

2-butyl-4-[(2'-carboxy-(1,1'-biphenyl-4-yl)-methyl)-6-ethoxy-5-pyrimidine acetic acid 1.46 g of the product of Example 7 were introduced into 15 ml of ethanol and 7.5 ml of 2N sodium hydroxide and the mixture was stirred at ambient temperature for 5 days, followed by evaporating to dryness under reduced pressure, dissolving in 50 ml of water, bringing the pH to approximately 5 by the addition of acetic acid, separating and washing with water. After drying, the mixture was stirred for 16 hours in 20 ml of water and separating, to obtain 1.03 g of the expected product melting at 105° C.

Analysis: C$_{26}$H$_{28}$N$_2$O$_5$; molecular weight = 448.52

| Calculated: | % C 69.63 | % H 6.29 | % N 6.25 |
|---|---|---|---|
| Found: | 69.5 | 6.3 | 6.1 |

IR Spectrum in chloroform:

| | |
|---|---|
| \>=O | 1710 cm$^{-1}$ |
| Conjugated system | 1599 cm$^{-1}$ |
| + | 1572 cm$^{-1}$ |
| Aromatics | 1568 cm$^{-1}$ |
| Absorption OH/NH region | |

EXAMPLE 13

Ethyl 2-butyl-1,6-dihydro-4-hydroxy-1-[4-methoxycarbonyl-benzyl]-6-oxo-5-pyrimidine acetate 100 mg of the product of Step D of Example 1 were introduced into 4 ml of dimethylformamide, 108 mg of potassium carbonate and 106 mg of [4-(methoxycarbonyl)-benzyl]-bromide. The mixture was stirred at ambient temperature for 6 hours, followed by pouring into water, extracting 3 times with ethyl acetate, washing with a saturated solution of sodium chloride and evaporating to dryness under reduced pressure. After chromatography on silica (eluant: methylene chloride-ethyl acetate: 6-4), 55 mg of the expected product melting at 170° C. were obtained.

IR Spectrum in chloroform:

| | |
|---|---|
| C = O | 1720 cm$^{-1}$ |
| | 1645 cm$^{-1}$ |
| Conjugated system | 1614 cm$^{-1}$ |
| + | 1600 cm$^{-1}$ |
| Aromatic | 1580 cm$^{-1}$ |
| | 1490 cm$^{-1}$ |

EXAMPLE 14

2-butyl-1-[(4-carboxyphenyl)-methyl]-1,6-dihydro-4-hydroxy-6-oxo-5-pyrimidine acetic acid 98 mg of the product of Example 13 were introduced into 3 ml of ethanol and 0.48 ml of 2N sodium hydroxide and the mixture was refluxed with stirring for 4 hours, then evaporated to dryness under reduced pressure. The residue was added to 4 ml of water, neutralized by the addition of 0.48 ml of 2N hydrochloric acid, separated and washed with water. After taking up in 4 ml of hot isopropanol with 0.4 ml of water added to it, it stood at rest for 16 hours, then separated to obtain 62 mg of the expected product melting at 260° C.

Analysis: C$_{18}$H$_{20}$N$_2$O$_6$; molecular weight = 360.37

| Calculated: | % C 59.99 | % H 5.59 | % N 7.77 |
|---|---|---|---|

| Found: | 60.3 | 5.6 | 7.6 |
|---|---|---|---|

IR Spectrum in NUJOL:

| $\rangle{=}O$ | 1716 cm$^{-1}$ |
|---|---|
| | 1674 cm$^{-1}$ |
| | 1653 cm$^{-1}$ |
| $-C=C$, $-C=N$ | 1603 cm$^{-1}$ |
| and | 1577 cm$^{-1}$ |
| aromatics | 1514 cm$^{-1}$ |

EXAMPLE 15

Ethyl 2-butyl-4-chloro-6-[[2'-cyano-(1,1'-biphenyl)-4-yl]-methyl]-5-pyrimidine acetate a) [[2'-cyano-(1,1'-biphenyl)-4-yl]-methyl]zinc bromide.

Using the procedure of Example 1, 457 mg of electrolytic zinc, 1 ml of tetrahydrofuran, 0.08 ml of 1,2-dibromoethane and 1.36 g of [[2'-cyano-(1,1'-biphenyl)-4-yl]-methyl]-bromide in 6.8 g of tetrahydrofuran were reacted.

b) Ethyl 2-butyl-4-chloro-6-[[2'-cyano-(1,1'-biphenyl)4-yl]-methyl]- 5-pyrimidine acetate Using the procedure of Example 1, 873 mg of the product of Step E of Example 1 were reacted with 8.7 ml of anhydrous tetrahydrofuran, 364 mg of tetrakis(triphenyl phosphine) palladium and 5.7 ml of a 0.5 M/l solution of the organozinc obtained in a) above. After chromatography on silica (eluant: methylene chloride-hexane 9-1 then hexane-ethyl acetate 6-4), 407 mg of the expected product melting at 66° C. were obtained.

Analysis: $C_{26}H_{26}N_3O_2Cl$; molecular weight = 447.97

| Calculated: | % C 69.91 | % H 5.85 | % Cl 7.91 | % N 9.38 |
|---|---|---|---|---|
| Found: | 70.0 | 6.0 | 8.1 | 9.1 |

IR Spectrum in chloroform:

| $\rangle{=}O$ | 1734 cm$^{-1}$ |
|---|---|
| $-C\equiv N$ | 2225 cm$^{-1}$ |
| Aromatic | 1598 cm$^{-1}$ |
| + | 1570 cm$^{-1}$ |
| conjugated system | 1528 cm$^{-1}$ |

EXAMPLE 16

Ethyl 2-butyl-4-chloro-6-[[2'-(1H-tetrazol-5-yl)-(1,1'-biphenyl)-4-yl]-methyl]-5-pyrimidine acetate 300 mg of the product of Example 15 were introduced into 6 ml of toluene in the presence of 205 mg of trimethyltin nitride and the mixture was refluxed for 24 hours. The mixture was poured into 30 ml of water and extracted with ethyl acetate. The organic phase was washed with a saturated aqueous solution of sodium chloride, dried and the solvent was eliminated under reduced pressure. After chromatography of the residue on silica (eluant: methylene chloride-methanol 95-5), 180 mg of product were isolated which was crystallized from ethyl acetate to obtain 94 mg of the expected product melting at 160° C.

Analysis: $C_{26}H_{27}N_3O_6Cl$; molecular weight = 490.99

| Calculated: | % C 63.60 | % H 5.54 | % Cl 7.22 | % N 17.11 |
|---|---|---|---|---|
| Found: | 63.7 | 5.5 | 7.1 | 17.3 |

IR Spectrum in chloroform:

| $\rangle{=}O$ | 1732 cm$^{-1}$ |
|---|---|
| $-NH$ + associated | 3404 cm$^{-1}$ |
| Aromatic | 1612 cm$^{-1}$ |
| + | 1600 cm$^{-1}$ |
| conjugated system | 1566 cm$^{-1}$ |
| | 1529 cm$^{-1}$ |

EXAMPLE 17

2-butyl-4-chloro-6-[[2'-(1H-tetrazol-5-yl)-(1,1'-biphenyl)-4-yl]methyl]-5-pyrimidine acetic acid 128 mg of the product of Example 16 were introduced into 2.56 ml of dioxane and 0.52 ml of 2N sodium hydroxide and the mixture was stirred at ambient temperature for 16 hours, then diluted with 10 ml of water, neutralized with 0.52 ml of 2N hydrochloric acid and evaporated to dryness under reduced pressure to obtain 135 mg of crude product which was crystallized from ethyl acetate and hexane to obtain 85 mg of the expected product melting at 180° C.

IR Spectrum in chloroform:

| $\rangle{=}O$ | 1700 cm$^{-1}$ |
|---|---|
| Aromatic | 1605 cm$^{-1}$ |
| + | 1564 cm$^{-1}$ |
| heterocycle | 1525 cm$^{-1}$ |

EXAMPLE 18

Pharmaceutical Composition

Tablets were prepared containing 10 mg of the product of Example 8 and sufficient (excipient of lactose, talc, starch, magnesium stearate) for a tablet weighing 100 mg.

PHARMACOLOGICAL RESULTS

Test on the Angiotensin II Receptor

A fresh membrane preparation obtained from rat's liver was used and the tissue was ground in a polytron in a Tris 50mMpH 7.4 buffer. The grinding was followed by 3 centrifugations at 30,000 g for 15 minutes with intermediate collection of pellets in the Tris buffer pH 7.4. The last pellets were suspended in an incubation buffer (Tris 20 mM, NaCl 135 nM, KCl 10 mM, glucose 5 mM, $MgCl_2$ 10 mM, PMSF 0.3 mM, bacitracin 0.1 mM, BSA 0.2%). The 2 ml of aliquoted fractions were distributed in hemolysis tubes and $^{125}$I angiotensin II (25,000 DPM/tube) and the product to be studied were added. The product was first tested at $3\times10^{-5}$M in triplicate. When the product to be tested displaced more than 50% of the radioactivity specifically linked to the receptor, it was tested again in a range of 7 concentrations to determine the concentration which inhibited 50% of the radioactivity specifically linked to the receptor. In this way, the 50% inhibiting concentration was determined.

The non-specific bond was determined by the addition of the product of Example 94 of the European Patent No. 0,253,310, at $10^{-5}$M (in triplicate). Incubation took place at 25° C. for 150 minutes, followed by returning to a water bath at 0° C. for 5 minutes, vacuum filtration, rinsing with Tris buffer pH 7.4 and counting the radioactivity in the presence of scintilling Triton. The result was expressed directly as 50% inhibiting concentration ($IC_{50}$), that is to say as a concentration of the studied product, expressed in nM, necessary to displace 50% of the radioactivity specifically fixed on the studied receptor.

Results:

| PRODUCT OF EXAMPLE | $IC_{50}$ in nM |
|---|---|
| 8 | 242 |

Various modifications of the products and method of the invention may be made without departing from the spirit or scope thereof and it is to be understood that the invention is intended to be limited only as defined in the appended claims.

What is claimed is:

1. A compound of the formula

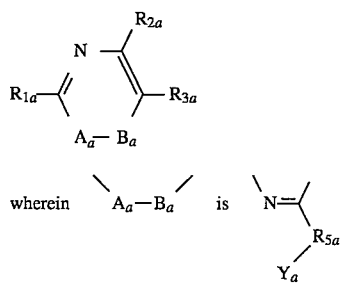

wherein $A_a$—$B_a$ is $\mathrm{N{=}\!\!\!<}^{R_{5a}}_{Y_a}$ $R_{5a}$ is a single bond or —$(CH_2)_m$—, $Y_a$ is biphenyl unsubstituted or substituted by at least one member of the group consisting of hydroxyl; halogen; alkyl and alkoxy of 1 to 4 carbon atoms; trifluoromethyl; cyano; nitro, amino; carbamoyl; free, salified or esterified carboxy; tetrazolyl; isoxazolyl; phenoxy; benzyl; $R_{1a}$ is selected from the group consisting of alkyl, alkenyl, alkynyl, alkylthio of up to 10 carbon atoms, or cycloalkyl of 3 to 7 carbon atoms, all unsubstituted or substituted by at least one member of the group consisting of halogen, hydroxyl, alkoxy of 1 to 6 carbon atoms, alkylthio, acyl, free, salified or esterified carboxy, formyl, cyano, nitro, amino unsubstituted or substituted by one or two individual alkyl of 1 to 6 carbon atoms, cyclo-alkyl of 3 to 7 carbon atoms and aryl unsubstituted or substituted by at least one member of the group consisting of halogen, hydroxyl, alkyl, alkenyl and alkoxy of up to 6 carbon atoms, haloalkyl, alkylthio, haloalkylthio, haloalkoxy, aryloxy, aryl-alkoxy, carbamoyl, acyl, acyloxy, free, salified or esterified carboxy, tetrazolyl, cyano, nitro, amino unsubstituted or substituted by at least one alkyl of 1 to 6 carbon atoms and phenyl unsubstituted or substituted by at least one member of the group consisting of halogen, hydroxyl, alkyl and alkoxy of 1 to 4 carbon atoms, trifluoromethyl, free, salified or esterified carboxy and tetrazolyl, $R_{2a}$ is chosen from the group consisting of hydrogen, halogen, hydroxyl, mercapto, cyano, nitro, formyl, benzoyl, acyl of 1 to 6 carbon atoms, alkyl, alkenyl, alkoxy, alkylthio of up to 10 carbon atoms, phenyl, phenoxy, naphthyl, benzyl, phenylthio, biphenyl, biphenylmethyl and indole, all unsubstituted or substituted by at least one member of the group consisting of halogen, hydroxyl, alkoxy of 1 to 4 carbon atoms, trifluoromethyl, cyano, acyl, formyl, free, salified or esterified carboxy, tetrazolyl, isoxazolyl and pyridyl and $R_{3a}$ is alkyl substituted with carboxy or esterified carboxy.

2. A compound of claim 1 wherein $Y_a$ is biphenyl unsubstituted or substituted by at least one of cyano, free, salified and esterified carboxy or tetrazolyl and $R_{1a}$ is ethyl, propyl, isopropyl, propen-1-yl, butyl, buten-1-yl, and $R_{2a}$ is selected from the group consisting of hydrogen, halogen, hydroxyl, phenyl, benzyl, biphenyl, biphenylmethyl, formyl, free, salified or esterified carboxy, alkyl, alkenyl, alkoxy and alkylthio of up to 6 carbon atoms unsubstituted or substituted by at least one member of the group consisting of halogen, hydroxyl, cyano, carboxy, free, salified or esterified by alkyl of 1 to 4 carbon atoms, alkoxy and alkyl of 1 to 4 carbon atoms, trifluoro-methyl, amino, mono- or dialkylamino, tetrazolyl and isoxazolyl.

3. A compound of claim 1 wherein $Y_a$ is biphenyl unsubstituted or substituted by at least one cyano, and tetrazolyl, $R_{1a}$ is n-butyl, $R_{2a}$ is selected from the group consisting of halogen, hydroxyl, alkoxy and alkyl optionally substituted by cyano, free, salified or esterified carboxy, free, salified or esterified by alkyl of 1 to 4 carbon atoms and tetrazolyl.

4. A compound of claim 1 which is 2-butyl-4-[(2'-carboxy-( 1,1'-biphenyl)-4-yl)-methyl]-6-chloro-5-pyrimidine acetic acid.

5. An angiotensin II inhibiting composition comprising an angiotensin II inhibiting effective amount of at least one compound of claim 1 and an inert pharmaceutical carrier.

6. A composition of claim 5 wherein the active compound is 2-butyl-4-[(2'-carboxy-(1,1'-biphenyl)-4-yl)-methyl]-6-chloro-5-pyrimidine acetic acid.

7. A method of inhibiting angiotensin II activity in warm-blooded animals comprising administering to warm-blooded animals an angiotensin II inhibiting effective amount of at least one compound of claim 1.

8. The method of claim 7 wherein the active compound is 2-butyl-4-[(2'-carboxy-(1,1'-biphenyl)-4-yl)-methyl]-6-chloro- 5-pyrimidine acetic acid.

* * * * *